(12) United States Patent
Nagao et al.

(10) Patent No.: US 9,474,817 B2
(45) Date of Patent: Oct. 25, 2016

(54) SYSTEMS AND METHODS FOR MONITORING AND COMPENSATING FOR BLEACH CONCENTRATION CHANGES

(71) Applicants: Blaine Nagao, Itasca, TX (US); Steve Dumler, Colleyville, TX (US)

(72) Inventors: Blaine Nagao, Itasca, TX (US); Steve Dumler, Colleyville, TX (US)

(73) Assignee: H2trOnics, Inc., Grapevine, TX (US)

( * ) Notice: Subject to any disclaimer, the term of this patent is extended or adjusted under 35 U.S.C. 154(b) by 531 days.

(21) Appl. No.: 13/960,505

(22) Filed: Aug. 6, 2013

(65) Prior Publication Data

US 2014/0044599 A1 Feb. 13, 2014

Related U.S. Application Data

(60) Provisional application No. 61/680,571, filed on Aug. 7, 2012.

(51) Int. Cl.
*A61L 2/24* (2006.01)
*A61L 2/18* (2006.01)

(52) U.S. Cl.
CPC .. *A61L 2/24* (2013.01); *A61L 2/18* (2013.01); *A61L 2202/14* (2013.01)

(58) Field of Classification Search
CPC ........ A61L 2/18; A61L 2/24; A61L 2202/14
See application file for complete search history.

(56) References Cited

U.S. PATENT DOCUMENTS

2011/0024361 A1* 2/2011 Schwartzel ............. C02F 1/325
210/739

* cited by examiner

*Primary Examiner* — Timothy Cleveland
(74) *Attorney, Agent, or Firm* — Kirby B. Drake; Klemchuk LLP

(57) ABSTRACT

Systems and methods for monitoring and compensating for bleach concentration changes within a disinfection system may be provided. A bleach concentration monitor may be introduced into a disinfection system to measure the percentage concentration of a bleach precursor that may be introduced into a mixer and then report the measurements to pump controls within the disinfection system. Data relating measurements of the concentration of the bleach precursor may be transmitted to pump controls within the disinfection system so that adjustments may be made to a control algorithm within the pump controls to compensate for any changes that may be observed related to bleach concentration in the system.

9 Claims, 1 Drawing Sheet

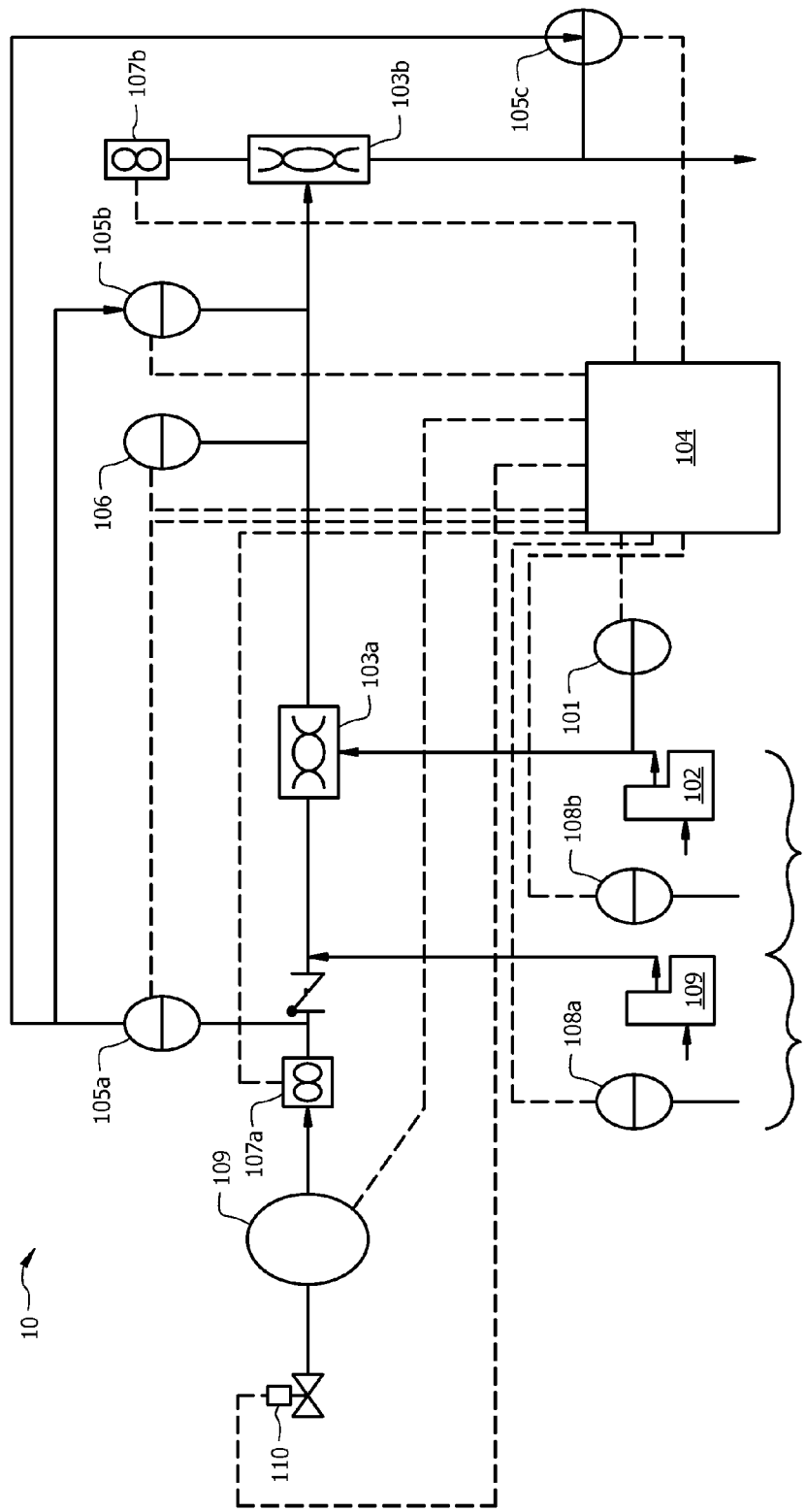

SYSTEMS AND METHODS FOR MONITORING AND COMPENSATING FOR BLEACH CONCENTRATION CHANGES

CROSS-REFERENCE TO RELATED APPLICATION

The present Application claims the benefit of U.S. Provisional Application No. 61/680,571 entitled "Systems and Methods for Monitoring and Compensating for Bleach Concentration Changes," filed Aug. 7, 2012, the disclosure of which is hereby incorporated by reference in its entirety.

FIELD OF THE DISCLOSURE

The present disclosure generally relates to systems and methods for monitoring and compensating for bleach concentration changes.

BACKGROUND

Disinfectants may be used in various industries to destroy microorganisms that may be living on surfaces, in water, and/or in the air. For example, a hydrogen bromide solution precursor may be activated with a sodium hypochlorite (bleach) precursor to act as a disinfectant in the food industry. Such a disinfectant may be prepared by adding the bromine source into a water flow and then introducing bleach into the water flow either before or after the bromine source has been added. In order to maintain a predetermined concentration for the disinfectant, total dissolved solids (TDS) sensors and a pH sensor may be used to monitor the concentration and/or rate of injection of the disinfectant components.

SUMMARY

Embodiments of the present disclosure may provide systems and methods for monitoring and compensating for bleach concentration changes within a disinfection system. A bleach concentration monitor may be introduced into a disinfection system to measure the percentage concentration of a bleach precursor that may be introduced into a mixer and then report the measurements to pump controls within the disinfection system. Data relating measurements of the concentration of the bleach precursor may be transmitted to pump controls within the disinfection system so that adjustments may be made to a control algorithm within the pump controls to compensate for any changes that may be observed related to bleach concentration in the system. Based on the feedback from the bleach concentration monitor, the TDS endpoint of the disinfection solution may be adjusted up or down to compensate for the changing concentration of the bleach precursor. This adjustment may be determined via a control system. As the concentration of the bleach precursor decreases, the speed of a hypobromous acid precursor pump may be increased relative to the change. The speed of a chlorine pump also may change based on the pH change imparted by the increased hypobromous acid precursor feed. As the concentration of the bleach precursor increases, the reverse may occur.

Embodiments of the present disclosure may provide a system for monitoring and adjusting bleach concentration within a disinfection system comprising a bleach concentration monitor placed in the proximity of and in communication with a chlorine pump to measure the bleach concentration of a disinfection solution leaving the chlorine pump and traveling to a mixer, wherein the bleach concentration monitor may transmit the bleach concentration measurements to pump controls, and the pump controls may use the bleach concentration measurements to adjust a total dissolved solids (TDS) endpoint of the disinfection solution. The system may further comprise at least one TDS sensor that monitors the concentration of the disinfection solution and transmits to the pump controls. The desired concentration levels for the at least one TDS sensor may be predetermined and set through the pump controls or may be set through manual pump adjustment at commissioning. The system may further comprise a pH monitor that measures the pH of the disinfection solution moving within the disinfection system. The bleach concentration may be monitored in real time or through periodic sampling. The disinfection system may further comprise a hypobromous acid precursor pump wherein as the bleach concentration decreases, the speed of the hypobromous acid precursor pump is increased. The speed of the chlorine pump may change based on the pH change imparted by the increase in the speed of the hypobromous acid precursor pump. As the bleach concentration increases, the speed of the hypobromous acid precursor pump is decreased.

Embodiments of the present disclosure may provide a method for monitoring and adjusting bleach concentration within a disinfection system comprising using a bleach concentration monitor, measuring the percentage concentration of a bleach precursor introduced into a mixer within the disinfection system, reporting the measurements from the bleach concentration monitor to pump controls within the disinfection system, and adjusting a total dissolved solids (TDS) endpoint of the disinfection system based on the measurements received by the pump controls to compensate for changes in the percentage concentration of the bleach precursor. The measuring step may occur in real-time or based on periodic sampling. The method also may comprise using a pH monitor, monitoring the pH of the disinfection system and reporting the pH to the pump controls. The method may further comprise using at least one TDS sensor, monitoring the concentration of a disinfection solution and transmitting measurements to the pump controls. The desired concentration levels for the at least one TDS sensor may be predetermined and set through the pump controls or may be set through manual pump adjustment at commissioning. The method may further comprise increasing the speed of a hypobromous acid precursor pump within the disinfection system as the percentage concentration of the bleach precursor increases. As the speed of the hypobromous acid precursor pump increases, the speed of the chlorine pump changes based on the pH change imparted by the increase in the speed of the hypobromous acid precursor pump.

BRIEF DESCRIPTION OF THE DRAWINGS

For a more complete understanding of this disclosure, reference is now made to the following description, taken in conjunction with the accompanying drawings, in which:

FIG. 1 depicts a disinfection system including a bleach concentration monitor according to an embodiment of the present disclosure.

DETAILED DESCRIPTION

Embodiments of the present disclosure may be directed to systems and methods for monitoring and compensating for bleach concentration changes within a disinfection system.

A correlation may be observed between the TDS of a disinfection solution and the parts per million (PPM) of hypobromous acid in the disinfection solution. The approximate PPM of the disinfection solution may be determined by subtracting the TDS of dilution water from the TDS of hypobromous acid/bleach solution. It should be appreciated that the correlation between the TDS of the solution and the PPM of hypobromous acid may vary depending on the concentration of bleach that may be utilized within a disinfection system. As the concentration of bleach decreases within a disinfection solution, the correlation between the TDS of the disinfection solution and the PPM of the hypobromous solution also may decrease. Accordingly, a bleach concentration monitor may be utilized to track the bleach concentration in order to make adjustments to the system as a whole.

A sodium hypochlorite (bleach) concentration monitor, such as the Optek AF26 or another bleach concentration monitor as may be known to one of ordinary skill, may be introduced into a disinfection system to track the concentration of a bleach precursor. It should be appreciated that the bleach concentration monitor may measure the percentage concentration of a bleach precursor that may be introduced into a mixer and then report the measurements to pump controls within the disinfection system. Data relating measurements of the concentration of the bleach precursor may be transmitted to pump controls within the disinfection system so that adjustments may be made to a control algorithm within the pump controls to compensate for any changes that may be observed related to bleach concentration in the system.

FIG. 1 depicts placement of bleach concentration monitor 101 within disinfection system 10 according to an embodiment of the present disclosure. Bleach concentration monitor 101 may be placed in the proximity of and in communication with chlorine pump 102 so as to measure the concentration of bleach leaving the area around chlorine pump 102 and traveling to mixer 103a. As bleach concentration monitor 101 takes measurements as to the bleach concentration, such as in real-time or based on periodic sampling as will be later described, those measurements may be transmitted to pump controls 104. It should be appreciated that the position of the monitor may vary as long as it is in the proximity of the pump to make measurements as have been described.

Based on the feedback from the bleach concentration monitor, the TDS endpoint of the disinfection solution may be adjusted up or down to compensate for the changing concentration of bleach precursor within the system. This adjustment may be determined via a control system, such as pump controls 104. As the concentration of the bleach precursor goes down, the speed of the hypobromous acid precursor pump, such as bromine pump 109, may be increased relative to the change. The chlorine pump, such as chlorine pump 102, also may change speed based on the pH change imparted by the increased bromine feed. As the concentration of the bleach precursor increases, the reverse may occur. The bromine pump speed may be initially set and the output may be verified by field-testing using standard methods of analysis.

Pump controls 104 also may receive measurements and/or data from other components in system 10, including but not limited to TDS sensors 105a, 105b, 105c as well as pH monitor 106, flow meters 107a, 107b, and tank level monitors 108a, 108b, according to embodiments of the present disclosure. The pH of the solution moving within disinfection system 10, such as from mixer 103a to mixer 103b, may be monitored through pH monitor 106. The rate of injection of bleach from chlorine pump 102 and/or bromine pump 109 may be adjusted to achieve a predetermined pH or pH range within system 10. TDS sensors 105a, 105b and/or 105c may monitor the concentration of the disinfection solution as it moves through disinfection system 10. The desired concentration levels for the TDS sensors to monitor may be predetermined and set through pump controls 104 according to an embodiment of the present disclosure. In other embodiments of the present disclosure, the TDS sensors may be set through manual pump adjustment at commissioning.

Additional components of system 10 also may communicate with pump controls 104 including but not limited to booster pump 109 and motive water control valve 110 as depicted in FIG. 1. While FIG. 1 depicts various components within system 10 communicating and/or providing measurements to pump controls 104, it should be appreciated that more or fewer components may communicate and/or provide measurements to pump controls 104 without departing from the present disclosure. Further, while the pump controls have been depicted in FIG. 1 in a single location within system 10, in some embodiments of the present disclosure, the pump controls may be dispersed within the disinfection system (i.e., be in more than one location within the system) and control different components of the system while communicating with each other.

While two mixers (103a, 103b) may be depicted in FIG. 1, it should be appreciated that more or fewer mixers may be included within a disinfection system without departing from the present disclosure. Similarly, while bromine pump 109 and chlorine pump 102 may be depicted in FIG. 1, it should be appreciated that other chemicals or solutions may be introduced in addition to or in place of bromine and chlorine for disinfection purposes according to embodiments of the present disclosure. Further, while the various components of a disinfection system have been depicted in a specific configuration in FIG. 1, it should be appreciated that the relative positions of the various components may be modified in terms of placement within the system or even inclusion within the system without departing from the present disclosure.

It should be appreciated that the concentration of the bleach precursor may be tracked in real time and/or through periodic sampling. In systems with low bleach demands, periodic sampling may be used due to the relatively long transmit time between a storage vessel and the generation apparatus. However, real time tracking may provide for more immediate detection of changes in concentration, and accordingly, adjustments may be made quicker in embodiments of the present disclosure. Real time tracking may be accomplished in line between the delivery apparatus and the injection point as well at the storage vessel according to embodiments of the present disclosure.

It should be appreciated that systems and methods according to embodiments of the present disclosure may be used for inline applications. It also should be appreciated that systems and methods according to embodiments of the present disclosure may be used in a variety of industrial applications, including but not limited to medical and food disinfection applications.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for monitoring and adjusting bleach concentration within a disinfection system, the method comprising:
    measuring the percentage concentration of a bleach precursor introduced into a mixer that leaves a chlorine pump within the disinfection system, wherein the percentage concentration is measured using a bleach concentration monitor, and wherein the bleach concentration monitor is in communication with the chlorine pump;
    reporting the measured percentage concentration from the bleach concentration monitor to pump controls within the disinfection system; and
    adjusting a total dissolved solids (TDS) endpoint of the disinfection system based on the measurements received by the pump controls to compensate for changes in the percentage concentration of the bleach precursor.

2. The method of claim 1 wherein the measuring step occurs in real-time.

3. The method of claim 1 wherein the measuring step occurs based on periodic sampling.

4. The method of claim 1 further comprising:
    using a pH monitor, monitoring the pH of the disinfection system and reporting the pH to the pump controls.

5. The method of claim 1 further comprising:
    using at least one TDS sensor, monitoring the concentration of a disinfection solution and transmitting measurements to the pump controls.

6. The method of claim 5 wherein desired concentration levels for the at least one TDS sensor are predetermined and set through the pump controls.

7. The method of claim 5 wherein desired concentration levels for the at least one TDS sensor are predetermined and set at commissioning.

8. The method of claim 1, further comprising:
    increasing the speed of a hypobromous acid precursor pump which pumps a hypobromous acid precursor within the disinfection system as the percentage concentration of the bleach precursor increases.

9. The method of claim 8 wherein as the speed of the hypobromous acid precursor pump increases, the speed of the chlorine pump changes based on the pH change imparted by the increase in the speed of the hypobromous acid precursor pump.

* * * * *